United States Patent
Aeschilimann et al.

(10) Patent No.: US 9,504,787 B2
(45) Date of Patent: Nov. 29, 2016

(54) INFUSION DEVICE WITH IMPEDANCE MEASUREMENT

(75) Inventors: Reto Aeschilimann, Aefigen (CH); James Leuenberger, Heimiswil (CH)

(73) Assignee: Roche Diagnostics International AG, Steinhausen (CH)

( * ) Notice: Subject to any disclaimer, the term of this patent is extended or adjusted under 35 U.S.C. 154(b) by 1951 days.

(21) Appl. No.: 12/641,911

(22) Filed: Dec. 18, 2009

(65) Prior Publication Data

US 2010/0160902 A1   Jun. 24, 2010

(30) Foreign Application Priority Data

Dec. 19, 2008   (EP) .................................... 08022099

(51) Int. Cl.
*A61K 9/22*   (2006.01)
*A61M 5/168*   (2006.01)
*A61B 5/053*   (2006.01)

(52) U.S. Cl.
CPC .......... *A61M 5/16836* (2013.01); *A61B 5/053* (2013.01); *A61M 5/16831* (2013.01); *A61B 5/0537* (2013.01); *A61M 2205/3317* (2013.01)

(58) Field of Classification Search
CPC .................... A61M 5/16836; A61M 5/16831; A61M 2205/3317
USPC ..................... 604/67, 891.1, 288.01–288.04, 604/174–175
See application file for complete search history.

(56) References Cited

U.S. PATENT DOCUMENTS

| | | | |
|---|---|---|---|
| 4,410,322 A | 10/1983 | Archibald | |
| 4,619,653 A * | 10/1986 | Fischell | 604/891.1 |
| 6,068,612 A | 5/2000 | Bowman et al. | |
| 6,142,008 A | 11/2000 | Cole et al. | |
| 6,159,186 A | 12/2000 | Wickham et al. | |
| 6,280,408 B1 | 8/2001 | Sipin | |

(Continued)

FOREIGN PATENT DOCUMENTS

| | | | |
|---|---|---|---|
| EP | 1 762 263 A1 | 3/2007 | |
| EP | 1 987 761 A1 | 11/2008 | |

(Continued)

OTHER PUBLICATIONS

PCT Partial International Search Report and Written Opinion dated May 11, 2011, PCT Application No. PCT/US2010/060949, filed Dec. 17, 2010.

(Continued)

*Primary Examiner* — Edelmira Bosques
(74) *Attorney, Agent, or Firm* — Dinsmore & Shohl LLP

(57) ABSTRACT

An ambulatory infusion device for the infusion of a liquid drug into a patient's body over an extended time period includes an infusion cannula designed to be placed in the patient's subcutaneous tissue. At least two subcutaneous electrodes are comprised by the infusion cannula and are placed in the subcutaneous tissue. An impedance measuring unit is operatively coupled to the at least two electrodes and is configured to measure at least one impedance value between the at least two electrodes. A variation of the at least one impedance value reflects a displacement of interstitial fluid by drug upon drug administration. An event trigger unit is operatively coupled to the impedance measuring unit and being configured to evaluate the at least one impedance value and to generate an event trigger if evaluation of the at least one impedance value indicates the occurrence of an administration anomaly.

15 Claims, 8 Drawing Sheets

(56) References Cited

U.S. PATENT DOCUMENTS

| | | |
|---|---|---|
| 6,464,667 B1 | 10/2002 | Kamen et al. |
| 6,475,178 B1 | 11/2002 | Krajewski et al. |
| 6,554,791 B1 | 4/2003 | Cartledge et al. |
| 6,558,346 B1 | 5/2003 | Yoshioka et al. |
| 6,616,633 B1 | 9/2003 | Butterfield et al. |
| 6,622,542 B2 | 9/2003 | Derek et al. |
| 6,623,455 B2 | 9/2003 | Small et al. |
| 2002/0016570 A1 | 2/2002 | Cartledge |
| 2002/0019612 A1 | 2/2002 | Watanabe et al. |
| 2003/0004463 A1 | 1/2003 | Reilly et al. |
| 2003/0040700 A1 | 2/2003 | Hickle et al. |
| 2003/0130616 A1* | 7/2003 | Steil et al. ............ 604/66 |
| 2003/0159741 A1 | 8/2003 | Sparks |
| 2003/0167035 A1 | 9/2003 | Flaherty et al. |
| 2004/0059295 A1 | 3/2004 | Cartledge et al. |
| 2004/0108226 A1* | 6/2004 | Polychronakos et al. .... 205/792 |
| 2004/0204673 A1 | 10/2004 | Flaherty |
| 2006/0206155 A1* | 9/2006 | Ben-David et al. .......... 607/9 |

FOREIGN PATENT DOCUMENTS

| | | |
|---|---|---|
| WO | 2006/027361 | 3/2006 |
| WO | 2006/113408 A2 | 10/2006 |
| WO | 2006/120253 A2 | 11/2006 |
| WO | 2007/128144 | 11/2007 |

OTHER PUBLICATIONS

International Search Report and Written Opinion dated Jul. 19, 2011 pertaining to International application No. PCT/US2010/060949, filed Dec. 17, 2010.

Office Action dated Jul. 14, 2011 pertaining to U.S. Appl. No. 12/646,501, filed Dec. 23, 2009.

Partial European Search Report, Appl. No. EP 08 020 2099, Search Date Jul. 13, 2009, 5 pages.

ACCU-CHEK Spirit Pump User Guide, Sep. 2008, pp. 1-202.

Species Election Requirement mailed May 26, 2011 as it relates to U.S. Appl. No. 12/646,501, filed Dec. 23, 2009.

* cited by examiner

INFUSION DEVICE WITH IMPEDANCE MEASUREMENT

CROSS-REFERENCE TO RELATED APPLICATIONS

This application claims the benefit of priority under 35 U.S.C. §119 of European Application No. 08022099.9, filed Dec. 19, 2008.

TECHNICAL FIELD

The present invention is related to ambulatory infusion devices for the infusion of a liquid drug into a patient's body over an extended time period, to corresponding infusion cannulas and to administration supervision methods for such ambulatory infusion devices.

BACKGROUND

Ambulatory infusion devices for the infusion of a liquid drug over an extended time period are used for a number of therapies. In particular, such devices form the basis for a state-of-the-art therapy of Diabetes Mellitus by CSII (Continuous Subcutaneous Insulin Infusion). Besides diabetes therapy, those devices may be used for a number of further therapies, such as cancer treatment or pain therapy, without requiring substantial modification. The following description mainly refers to CSII therapy by insulin infusion without being limiting to this specific application.

While present ambulatory infusion devices may be comparably comfortable, easy to use and robust, a number of malfunctions and error situations are known to occasionally occur, partly resulting from device defectives, and partly from handling errors. Those situations are, among others, leakages of the drug reservoir or the infusion tubing, occlusions, and a flow-back of administered insulin along the cannula and out of the subcutaneous tissue. While some of these conditions, in particular occlusions, may typically be detected by pre-sent ambulatory infusion devices with a generally undesired delay, some others, such as leakages or a drug flow-back, may not be detected at all by current devices. All of such events are in the following referred to as "administration anomalies".

SUMMARY

It is an objective of one or more embodiments of the present invention to improve the detection of such undesired conditions and to generally supervise the drug administration of ambulatory infusion devices. This goal may be achieved based on the insight that operation of the ambulatory infusion device may be supervised by measuring and evaluating at least one impedance value between at least two electrodes, wherein at least one or more of the electrodes are a subcutaneous electrode comprised by the infusion cannula. Correct operation of the infusion device as well as typical administration anomalies are reflected by the at least one impedance value or its variation with respect to time and/or position.

In one aspect, an ambulatory infusion device for the infusion of a liquid drug into a patient's body over an extended time period, comprising:
a) an infusion cannula designed to be placed in the patient's subcutaneous tissue;
b) at least two subcutaneous electrodes, the at least two subcutaneous electrodes being comprised by the infusion cannula and being placed in the subcutaneous tissue;
c) an impedance measuring unit, the impedance measuring unit being operatively coupled to the at least two electrodes and configured to measure at least one impedance value between the at least two electrodes, a variation of the at least one impedance value reflecting a displacement of interstitial fluid by drug upon drug administration;
d) an event trigger unit operatively coupled to the impedance measuring unit and being configured to evaluate the at least one impedance value and to generate an event trigger if evaluation of the at least one impedance value indicates the occurrence of an administration anomaly.

Here and in the following, the term "impedance" is generally used in the sense of an electrical impedance which may comprise ohmic, as well as capacitive and/or inductive components. Accordingly, the term "impedance value" generally refers to a complex value or a vector of values reflecting either or all of the impedance components. In some embodiments, the impedance is an ohmic resistance and the corresponding impedance value is a resistor value. However, capacitive and/or inductive impedance components may be evaluated alternatively or additionally to an ohmic impedance component. The term "impedance value" may further be referred to as a value correlated with and derivable from an impedance or impedance component, such as a specific conductivity, capacity, or the like as well as to an electrical measuring value correlated with an impedance or impedance component, such as the voltage drop over an impedance. The impedance is especially defined by the subcutaneous tissue and/or the drug which is administered by the infusion device.

The term "subcutaneous electrode" refers to an electrode which is placed in the subcutaneous tissue. Such a subcutaneous electrode may be arranged inside the infusion cannula or at the outer surface of the infusion cannula in an area which is placed in the subcutaneous tissue during application.

In some embodiments, the electrodes are, completely or partly, coated by substantially inert layers of gold, silver, platinum, or the like and/or may be made from substantially inherent materials. Further aspects and arrangements of the at least two electrodes will become apparent below.

One or more embodiments of the present invention may be understood based on a consideration of the subcutaneous tissue impedance, in particular the specific ohmic resistance of the subcutaneous tissue and of the drug. The specific ohmic resistance of the subcutaneous tissue and, thus, the ohmic resistance which may be measured between two electrodes placed in the subcutaneous tissue is under normal conditions largely given by the specific ohmic resistance of the interstitial fluid. The specific ohmic conductivity, i.e., the reciprocal of the specific ohmic resistance, of the interstitial fluid is about 15.8 mS/cm. The specific ohmic conductivity of insulin formulations and a number of further liquid drugs is about 2 mS/cm, that is, several times smaller as compared to interstitial fluid.

In a stationary state with no drug being administered or having been administered for some time, the specific impedance and in particular the specific ohmic resistance of the subcutaneous tissue is largely determined by interstitial fluid. If drug is administered, the interstitial fluid is, at least partly, temporarily displaced by drug in an area around the administration aperture at the distal tip of the infusion cannula, the drug forming a subcutaneous drug depot. Accordingly, the specific impedance and in particular the specific ohmic resistance of the subcutaneous tissue around the infusion cannula shows a temporary variation, the temporary variation especially involving a temporary increase and a peak in the specific ohmic resistance. After completing the administration, the specific impedance returns to its initial value along with the drug being absorbed by the subcutaneous tissue. Variation of the specific impedance with respect to time is reflected by a corresponding variation of a impedance value measured between two subcutaneous electrodes which are located at fixed positions in the subcutaneous tissue.

In addition, the drug concentration during and immediately after administration decreases with increasing distance from the administration aperture. During and immediately after drug administration, the specific impedance of the subcutaneous tissue is therefore non-uniform with respect to position. The specific ohmic resistance decreases with increasing distance from the administration aperture. Accordingly, the specific ohmic resistance or any component of the tissue impedance may therefore be considered as scalar field having a specific impedance gradient.

In the case of no impedance gradient, that is, in case of a uniform spatial impedance distribution, the impedance value measured between two subcutaneous electrodes is substantially proportional to the distance between the electrodes. This is not the case if an impedance gradient is present, that is, for a non-uniform spatial impedance distribution. The specific impedance variation along a given axis may therefore be determined by measuring impedance values between at least three electrodes of given distances placed along the given axis. Variation of the specific impedance along the axis is reflected by the impedance values measured between pairs of the at least three electrodes not being proportional to the distance between the electrodes. As will be described below, the axis may advantageously be the cannula axis. For simplicity reasons, the term "impedance distribution" is used in the following for the spatial distribution of the specific impedance of the subcutaneous tissue.

The variability of the specific impedance with respect to time and/or position may be evaluated for administration supervision and administration anomaly detection as described in the following. If, for any reason such as an occlusion, a leakage, a disconnected infusion cannula, a device fault, or the like, the drug is not administered, this variability will not occur.

In some embodiments, the impedance measuring unit therefore is designed to monitor the at least one impedance value as a function of time and/or position and the event trigger unit is designed to generate an event trigger if the at least one impedance value as a function of time and/or position indicates the occurrence of an administration anomaly.

In some embodiments, the event trigger unit is designed to generate an event trigger if the at least one impedance value indicates that a single drug administration, in particular a single basal drug pulse, has not been administered.

In some embodiments, the infusion device is designed to administer consecutive drug pulses and the event trigger unit is designed to generate an event trigger if the impedance value evaluation indicates that a predefined number of consecutive drug pulses have not been administered.

The drug pulses may especially be basal drug pulses which are administered according to a basal administration schedule. For small drug amounts, such as basal drug pulses, a number of administrations may not be performed as scheduled even in the absence of an error or a malfunction. Especially for ambulatory infusion devices of the syringe-driver type, the actual administration via the subcutaneous cannula may somewhat deviate from the theoretical administration schedule or regime. This is due to the fact that in particular for small administration rates involving very small drug pulses which typically are in the nano liter range, the plug of a drug cartridge may stick for a number of administrations, such that operation of the drive unit results in the plug tension being increased without actually moving the plug and thus without drug administration. At some point in time, however, the force exerted on the plug will result in the sticking being released, such that a drug pulse is administered.

Therefore, the event trigger unit may not generate an event trigger if a single drug administration, in particular a single basal drug pulse, is not administered as scheduled. If however, the number of consecutive basal drug pulses which is not administered exceeds a maximum number which can be expected due to sticking, an administration anomaly is likely to be present.

The event trigger unit may comprise a missed pulse counter, the missed pulse counter being designed to count the number of consecutive drug administrations or basal drug pulses which are not administered and to generate an event trigger only if the missed pulse number exceeds a missed pulse number threshold. The missed pulse number threshold may, for example, be in the range of three to five basal drug pulses. In some embodiments, the event trigger unit is designed to select the missed pulse number threshold in dependence of the basal administration rate and thus the drug amount of the basal drug pulses. For a small basal administration rate involving small plug motion increments, the missed pulse number threshold may be larger than for a large basal administration rate involving larger plug motion increments. Appropriate missed basal pulse number thresholds may be determined by a person skilled on the art based on the characteristics of the drive system of the infusion device and the characteristics of the drug reservoir. For this kind of embodiments, the term 'absence' in the context of a impedance variation with respect to time and/or position refers to the absence of a sequence of consecutive drug administrations rather than a single drug administration, in particular a basal drug pulse. Rather than administering basal drug pulses according to a predefined and static schedule, the infusion device may also be designed to administer basal drug pulses according to an adaptive schedule based, e.g. on continuous glucose measurements, with appropriate control algorithms being known in the art.

In a further modification of this type of embodiment, the event trigger unit is designed to generate an event trigger if the impedance value evaluation indicates that a predefined number of administrations was not performed as scheduled for drug pulses exceeding a given minimum drug pulse amount and not to generate an event trigger for a drug pulse amount below the given minimum drug pulse amount. This type of embodiment may prevent false alarms if the pulse amount of the basal drug pulses is too small to securely detect their administration.

After the administration of a basal drug pulses, the time required for the tissue to absorb the drug is typically in the range of seconds. For drug boli which are substantially larger, the time for the absorption and thus the time required for an impedance value to return to its initial value may be in the range of a minute or even longer. In addition, the variation of the specific tissue impedance and, thus, of the measured impedance values is larger for boli. Since boli may be administered at any time on demand, the impedance value variation resulting from a bolus administration and an impedance value variation resulting from a subsequent basal administration may be superimposed. In this case, the impedance value variation resulting from the basal administration may be too small to be detected. The event trigger unit may therefore be designed not to monitor an impedance value variation resulting from basal administration for a predefined dead time following a bolus administration.

In further embodiments, the event trigger unit is designed to generally only generate an event trigger if a drug bolus was not administered.

In some embodiments, the infusion device and/or a further device operatively coupled to the infusion device are designed to generate an alarm upon an event trigger being generated by the event trigger unit. The alarm may be generated via a user interface and may comprise an optical indication via, for example, a display, as well as an acoustical indication via a buzzer or the like and/or a tactile indication via a pager vibrator or the like. Further devices which may generate an alarm are remote controllers of the infusion device, cell phones, or the like. Alternatively or additionally to generating an alarm, event triggers may be stored in an event history of the infusion device and/or a further device for subsequent evaluation and/or record keeping purposes.

The impedance measuring unit may be of any kind known in the art, and comprise, for example, a reference voltage and/or reference current supply, voltage and/or current measurement circuitry, one or multiple analogue-to-digital converters, analogue and/or digital filters, and the like.

In some embodiments, the impedance measuring unit is designed to monitor at least one ohmic resistance value as impedance value, but may additionally or alternatively be designed to monitor other components of the at least one impedance value, in particular a capacitive and/or inductive impedance component using setups and methods known in the art. In some embodiments, the impedance measuring unit is designed for determining the at least one impedance value based on a four-wire measurement setup to enhance precision.

In some embodiments, the impedance measuring unit and the event trigger unit are designed to be operated continuously. In some embodiments, however, the impedance measuring unit and may also the event trigger unit are designed to be operated discontinuously. Discontinuous operation may be controlled by a controller unit of the infusion device or by one or multiple timers comprised by the impedance measuring unit and/or the event trigger unit. Discontinuous operation involves the advantages of reducing the power consumption and of limiting the electrical field exposure of the subcutaneous tissue.

In the framework of CSII and some further applications, the ambulatory infusion device is typically designed for quasi continuous drug administration according to a basal administration regime. This quasi continuous drug administration is performed by current insulin pumps of the syringe driver type in a pulsed manner, with a small drug pulse being administered with a fixed or variable time interval of typically some minutes. Typical ambulatory infusion devices for CSII therapy are further designed to administer drug boli on demand. Therefore, the impedance measuring unit and/or the event trigger unit may especially be operated for the drug administration, that is, in a limited time interval before, and/or during, and/or a limited time interval after administration of a drug pulse and/or a drug bolus.

If only ohmic resistance values are monitored, the impedance measuring unit may be designed to operate with DC measurement current and/or voltage. In some embodiments, however, the impedance measuring unit is designed to operate with AC measurement current and/or voltage. Such an arrangement avoids electrolysis of the subcutaneous tissue and avoids or at least minimizes electro-chemical reactions at the electrodes. The corresponding measurement frequency is advantageously in the range from 100 Hz to 100 KHz. The measurement frequency may especially be in the range from 1 KHz to 10 KHz. The impedance measuring unit may further be designed for impedance measurement selectively, in parallel or sequentially with more than one measurement frequency.

The at least one impedance value may show some patient specific variation and may further depend on factors such as temperature, cannula position in the tissue and application time from placing the subcutaneous cannula with the at least one subcutaneous electrode in the tissue. In CSII therapy, a subcutaneous cannula is used for a number of days and is afterwards replaced by a new cannula at a different location. A further offset component results from present electrical connectors, such as plugs which may be used to couple the electrodes to the impedance measuring unit. The impedance measuring unit may therefore be designed to determine an offset or bias after placing the subcutaneous cannula in the subcutaneous tissue. This offset or bias may subsequently be considered for determining the at least one impedance value.

Additionally or alternatively, the impedance measuring unit may compensate a drift of the at least one impedance value over time by correcting the offset or bias based on a look-up table, a mathematical formula describing the drift characteristics over time, and/or from the measured impedance values. A drift may occur due to increasing tissue irritation over the application time of the subcutaneous cannula and/or due to electrochemical and/or chemical reactions, such as corrosion, at the electrodes. For this purpose, reference impedance values may be measured at given points in time, such as once a day, once an hour, or the like and further measurements may be made with respect to those references. Besides directly using those measured values, the impedance measuring unit and/or the event trigger unit may be designed to compute a continuous interpolation or regression curve as a function of time and to employ the values of this curve as reference.

A further approach for avoiding or minimizing drift effects is to monitor and evaluate impedance value differences with respect to time and/or position rather than absolute values. This is advantageous in two respects: First, the incremental drift occurring in a short period of time, such as 1 second or a few minutes, is typically negligible. Second, drift effects electrodes placed at different positions in the subcutaneous tissue in the same way. Accordingly, difference measurements are largely drift independent.

In some embodiments involving monitoring and evaluating the at least one impedance value as a function of time, the event trigger unit is designed to detect the presence or absence of a characteristic temporary impedance value variation upon drug administration and to generate an event trigger in case of the absence of the temporary impedance value variation.

The event trigger unit may detect the presence or absence of the temporary impedance value variation by evaluating the at least one impedance value measured at different points in time, before, during, and/or after the drug administration. For this purpose, the event trigger unit may store a set of reference impedance values or reference impedance value ranges which are expected to be measured at different points in time before, during, and/or after drug administration. The event trigger unit may compare the impedance values with these reference impedance values or value ranges, respectively. Additionally or alternatively, the impedance evaluation unit may determine impedance value differences and/or impedance value ratios of impedance values measured at different points in time. Additionally or alternatively, a slope or change rate of impedance values may be evaluated.

The event trigger unit may further detect an temporary increase of the coupling impedance value by detecting if the at least one impedance value temporarily exceeds an threshold impedance value. Such a threshold value may be an absolute value or may be defined with respect to an offset impedance value or a value of a reference impedance curve as described above. All reference values, value reference ranges and thresholds may be selected depending on the drug type as well as the drug amount that is administered by routine experiments and/or computation. A dependency of those values on the drug amount may be stored in the event trigger unit in the form of formulas, a look-up table, or the like.

In some embodiments, the ambulatory infusion device comprises subcutaneous center electrode and a subcutaneous counter electrode, the subcutaneous center electrode being arranged in the center of an administration aperture of the infusion cannula and the subcutaneous counter electrode being arranged at the infusion cannula in an distance from the subcutaneous center electrode.

In some embodiments, the subcutaneous center electrode is arranged at or close to the distal tip of the infusion cannula.

Here and in the following, the terms "proximal" and "distal" are generally referred to with respect to the flow direction of the drug to be administered, wherein the term "proximal" refers to "upstream" and the term "distal" refers to "downstream". For the infusion cannula, the proximal end is the end projecting out of the skin and being connected to the infusion tubing. The distal end is the tip end of the infusion cannula as measured along the cannula axis. While other designs may be employed as well, it may be generally assumed that the distal tip of the infusion cannula is open, thus making the administration aperture. This is the case for typical infusion or injection cannulas as known in the art.

In some embodiments, the subcutaneous counter electrode is a further center electrode such that the center electrode and the counter electrode are arranged in axial alignment with the distance being an axial distance along the cannula axis. The distance may, for example, be in the range of 0.05 mm to 0.5 mm.

In some embodiments, the subcutaneous counter electrode is radially displaced with respect to the subcutaneous center electrode. If the infusion cannula is made from a conductive material, such as medical grade stainless steel, the infusion cannula itself advantageously serves as subcutaneous counter electrode with the distance being given by the radial distance of the subcutaneous center electrode surface and the infusion cannula inner surface. Alternatively, the infusion cannula is made from a non-conductive material, such as Teflon. In this case, the subcutaneous counter electrode may be arranged on at least one of the infusion cannula outer surface and the infusion cannula inner surface by means of coating, bonding, or the like. For this type of embodiment, the subcutaneous counter electrode may be a ring or a ring section circumferentially arranged at least at one of the infusion cannula outer surface and the infusion cannula inner surface. The subcutaneous counter-electrode may be arranged in axial alignment with the subcutaneous center electrode along the cannula axis. In a further alternative, either or both of the subcutaneous electrodes are arranged at the distal end surface, i.e., at the distal end surface of the cannula wall of a non-conductive infusion cannula.

In some embodiments, the ambulatory infusion device comprises a set of at least three subcutaneous electrodes. At least two impedance values may be measured between the at least three subcutaneous electrodes.

Since the subcutaneous tissue impedance gradient resulting from drug administration as described above has a component along the cannula axis, a non-uniform impedance distribution may advantageously be determined by monitoring and evaluating differences of impedance values along the cannula axis. Therefore, the at least three electrodes may be comprised by the infusion cannula at different positions along the cannula axis.

The spatial resolution of the impedance gradient component along the cannula axis increases with the number of subcutaneous electrodes. The number of subcutaneous electrodes may be in the range of 3 up to 10 and is in the range from 3 to 7 in some embodiments.

In some embodiments, the subcutaneous electrodes are rings or ring sections as described above. The subcutaneous electrodes are advantageously arranged in pair wise equal axial distance along the cannula axis. A most proximal subcutaneous electrode may be arranged at or close to the proximal end of the infusion cannula, such that it is placed in the patient's skin or in the subcutaneous tissue close to the skin. A most distal subcutaneous electrode may be arranged at or close to the distal tip and the administration aperture of the infusion cannula.

However, other arrangements of the subcutaneous electrodes may be used as well. For example, a pair of proximal subcutaneous electrodes may be arranged at or close to the proximal end of the infusion cannula, such that a proximal impedance value can be measured between the two proximal subcutaneous electrodes. Similarly, a pair of distal subcutaneous electrodes may be arranged at or close to the distal tip of the infusion cannula with the administration aperture such that a distal impedance value can be measured between the two distal subcutaneous electrodes. For this kind of embodiment, an approximation of the impedance gradient component along the cannula axis and thus the non-uniform impedance distribution may be derived from the difference and/or ratio of the proximal coupling impedance and the distal coupling impedance.

In some embodiments, the impedance measuring unit is designed to measure at least two impedance values between the at least three subcutaneous electrodes.

In some of those embodiments, the impedance values are measured between pair wise neighboring subcutaneous electrodes. Alternatively, the impedance measuring unit may be designed to use one of the subcutaneous electrodes as reference electrode and measure the impedance values between all other subcutaneous electrodes and the reference electrode. The impedance measuring unit may be designed to either determine all impedance values simultaneously or in a sequential way by scanning the electrodes.

In some embodiments, the event trigger unit is designed to detect if the at least two impedance values indicate the presence of a characteristic non-uniform impedance distribution along the cannula axis resulting from drug administration and to generate an event trigger if the at least two impedance values indicate the absence of the characteristic non-uniform impedance distribution.

Distinguishing between a uniform and non-uniform impedance distribution may be detected by the event trigger unit based by comparing the at least two impedance values.

The absence of a characteristic non-uniform distribution of the tissue impedance along the cannula axis may have two distinguishable reasons: If the drug is not administered for any reason, the impedance distribution is substantially uniform and determined by the interstitial fluid. If a flow-back of administered drug along the cannula axis and out of the patient's body occurs, the interstitial fluid will be largely displaced by drug along the whole cannula axis. Accordingly, the impedance distribution is substantially uniform and determined by the drug. The problem of flow-back is especially known for the administration of large drug volumes in a short time, such as large insulin boli.

Therefore, the event trigger unit may detect, in case the at least two impedance values indicate a substantially uniform impedance distribution along the cannula axis, if the measured impedance values correspond to the interstitial fluid or the drug. As stated above, the ohmic resistances between the subcutaneous electrodes are substantially higher in the latter case which is characteristic for a flow-back. For this type of embodiment, the event trigger unit may generate the event trigger such that the event trigger indicates which of the cases applies such that a missing administration on the one hand and a flow-back on the other hand and may be distinguished. Distinction may be performed by comparing the at least two impedance values with reference values or reference value ranges which are characteristic for the interstitial fluid and drug, respectively.

In some embodiments, the ambulatory infusion device comprises an upstream electrode arranged upstream from the infusion cannula.

In this type of embodiment, a subcutaneous electrode may, for example be a subcutaneous center electrode or a ring-shaped subcutaneous electrode as described above. The upstream electrode is arranged in direct contact with the drug. It may be arranged, for example, in a present drug reservoir or inside an adapter or connector coupling the infusion tubing and the drug reservoir. During normal operation, the impedance value measured between a subcutaneous electrode and the upstream electrode is largely defined by the drug. An air bubble in the fluid line or a particle, such as a silicone particle, in the fluid path results in a considerably higher or even substantially infinite resistance in series with the drug. The same effect occurs in case of the infusion tubing being interrupted or disconnected. The event trigger unit is therefore advantageously designed to detect the occurrence of this situation and generate an event trigger accordingly.

In a further aspect, the invention is directed towards the use of an infusion cannula in an ambulatory infusion device as described above for subcutaneous drug infusion over an extended time period. The infusion cannula comprises at least two subcutaneous electrodes.

In a still further aspect, the disclosure is related to a method administration supervision in an ambulatory infusion device for subcutaneous drug infusion over an extended time period, comprising the steps of:

a) measuring by an impedance measuring unit at least one impedance value between at least two subcutaneous electrodes, the at least two subcutaneous electrodes being comprised by an infusion cannula, a variation of the at least one impedance value reflecting a displacement of interstitial fluid by drug upon drug administration;

b) generating by an event trigger unit an event trigger if an evaluation of the at least one impedance value indicates the occurrence of an administration anomaly.

In some embodiments, the method comprises generating an event trigger if the impedance value evaluation indicates that a predefined number of consecutive drug pulses has not been not administered.

In some embodiments, the method comprises detecting the presence of a characteristic temporary impedance value variation upon drug administration and generating an event trigger in case of the absence of the temporary impedance value variation.

In some embodiments, the method comprises detecting the presence of a characteristic non-uniform impedance distribution along the cannula axis resulting from drug administration and generating an event trigger in case of the absence of the characteristic non-uniform impedance distribution.

Further aspects of the method for administration supervision may be directly derived from one or more embodiments of an infusion device according to the present invention.

In the following, exemplary embodiments of the present invention are described in greater detail with reference to the figures. The exemplary administration devices may be used in the framework of diabetes therapy by CSII and show functions and features known in the art for such infusion devices, for example from the Accu-Chek® Spirit insulin pump manufactured by Disetronic Medical Systems AG, Switzerland, and corresponding infusion cannulas, without further mentioning.

In the following, main focus is on infusion devices. However, exemplary embodiments of methods for administration supervision according to the present invention may be derived from those in a straight-forward manner.

BRIEF DESCRIPTION OF THE DRAWINGS

The structure and function of many elements is substantially or fully equivalent for some or all of the exemplary embodiments. Those elements are further referred to with the same reference number and are described in detail only where they are first mentioned.

DETAILED DESCRIPTION

Figure 1:
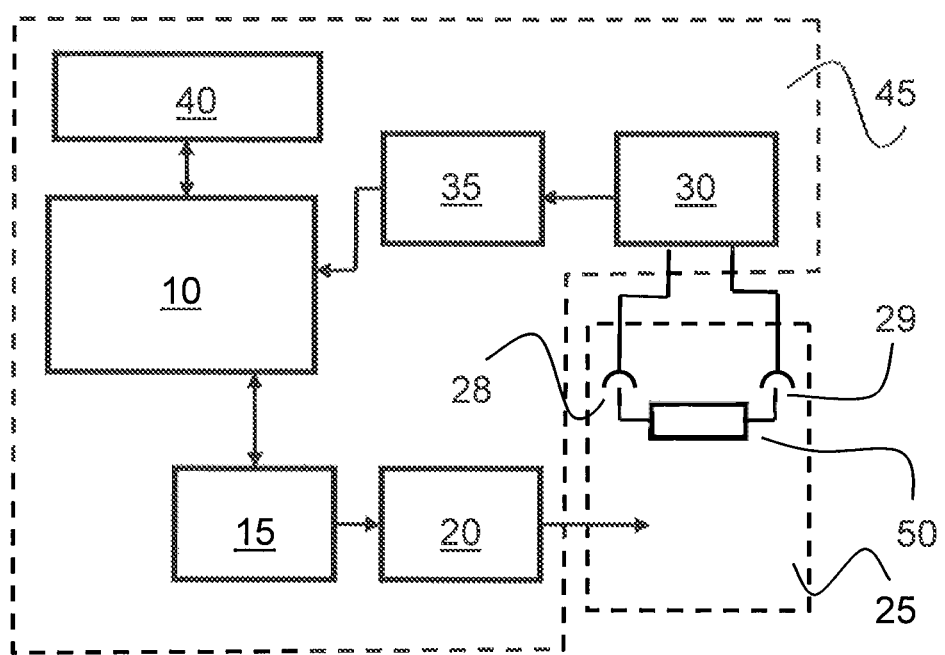
FIG. 1 shows a schematic structural view of an exemplary infusion device according to one or more embodiments of the present invention.
Figure 2:
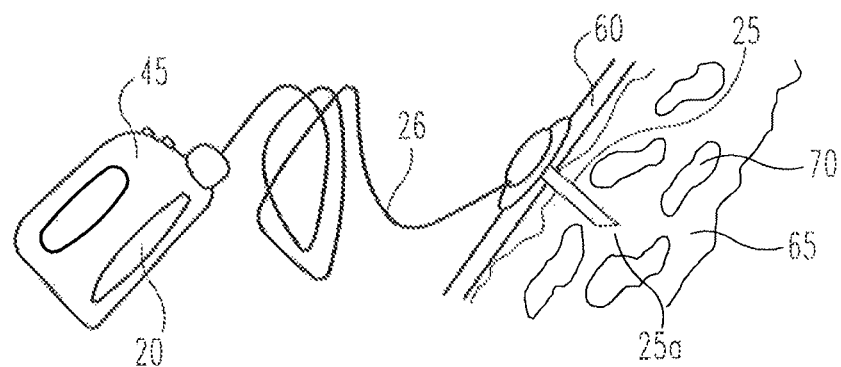
FIG. 2 schematically shows an infusion device according to one or more embodiments of the present invention during application.

In the following, reference is first made to FIG. 1 and FIG. 2, showing an exemplary infusion device. The infusion device comprises a controller unit 10, a drive system 15, a drug reservoir 20, an infusion cannula 25 with the distal cannula tip 25a, an impedance measuring unit 30, an event trigger unit 35 and a user interface 40, the user interface 40 being designed to indicate alarms. The term 'infusion cannula' mainly refers to its subcutaneous portion which is of major importance in the context of the present invention. However, the infusion cannula typically further comprises elements which are placed outside the skin during application, such as a plaster, a hub, an infusion tubing connector, or the like.

The infusion cannula 25 is made of medical grade stainless steel and is fluidic connection with the drug reservoir 20 via the infusion tubing 26. The cannula further comprises two subcutaneous electrodes 28, 29 as electrodes which are coupled via a coupling impedance 50 having an impedance value R as described below in further detail. As in the further examples described below, the coupling impedance is not an electric component but is given by the drug and/or subcutaneous tissue coupling the electrodes. The electrodes 28, 29 are operatively coupled to the impedance measuring unit 30. For coupling the electrodes 28, 29, the infusion cannula 25 may comprise electrical wires and/or connectors (not shown) which may be integral with the infusion tubing 26.

The impedance measuring unit 30 is designed to measure an ohmic resistance as impedance value R and may be of any kind known in the art as described in the general description of the invention. The impedance measuring unit 30 is operatively coupled to the event trigger unit 35 which is designed to evaluate the impedance value R and generate an event trigger as described below in greater detail. Either of both of the impedance measuring unit 30 and the event trigger unit 35 may be, fully or partly, integral with the controller unit 10.

Upon reception of an event trigger generated by the event trigger unit 35, the controller unit 10 generates an alert or error message and/or a warning which is indicated to the user via the user interface 40 and may stop further drug administration. The user interface 40 may comprise optical indicators, such as a display as well as acoustical and/or tactile indicators, such as a buzzer and/or a pager vibrator.

The ambulatory infusion device may further comprise components and elements not shown in FIG. 1 but obvious for a person skilled in the art such as communication interfaces and a power supply.

Most of the components of the exemplary infusion device are enclosed by a common device housing 45. Alternatively, the infusion device may be split into two or more separated units which are physically and/or operatively coupled. For example, the user interface 40 may be made by a remote controller, a cell phone, or the like, and may communicate with the controller unit via a wireless data interface. Similarly, the impedance measuring unit 30 and/or the event trigger unit 35 may be integral with the cannula 25. In some embodiments, the infusion cannula 25 directly projects out of the device housing 45 without requiring fluidic tubing and/or electrical wires.

The infusion cannula 25 penetrates the skin 60 in a substantially perpendicular manner and is placed in the subcutaneous tissue 65, the subcutaneous tissue 65 having interstitial fluid 70. The infusion tubing 26 is comprised by the infusion cannula 25 and provides both fluidic and electric coupling. Instead of the infusion cannula 25 being substantially perpendicular to the skin 60, the infusion cannula may be inserted with a smaller angle of, e.g., 10° to 20°.

Figure 3:
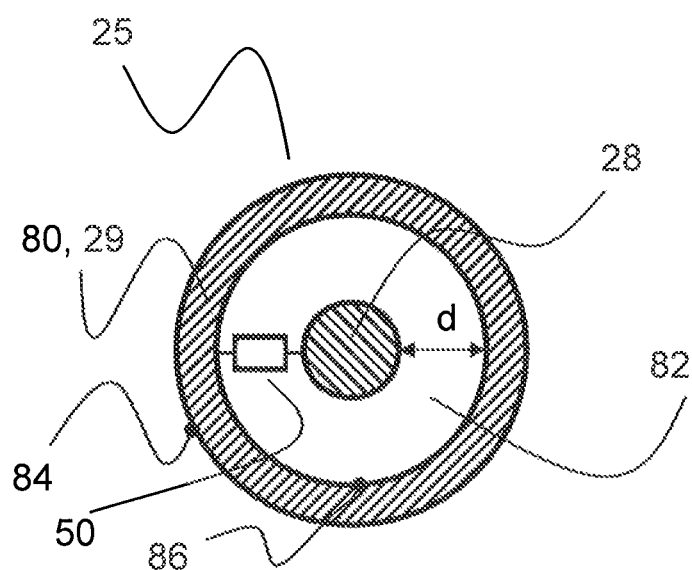
FIG. 3 schematically shows a cross-sectional view of the subcutaneous portion of the infusion cannula according to FIG. 2.

FIG. 3 shows a cross sectional view of the infusion cannula 25, substantially being a cylindrical tube having a cannula wall 80 and an administration aperture 82 at its distal tip 25a. The electrode 28 is a subcutaneous center electrode and is arranged in the center of the administration aperture 82. The second electrode 29 is a subcutaneous counter electrode which is made by the cannula wall 80. The subcutaneous center electrode 28 and the subcutaneous counter electrode 29 have a radial distance d which may be in a range of e.g., 0.05 mm to 0.5 mm. Alternatively, the cannula 25 may be made from a non-conductive material, such as Teflon. In this, case, the subcutaneous counter electrode 29 may be designed as ring or ring segment and arranged at the cannula outer surface 84 or the cannula inner surface 86.

Figure 4A:
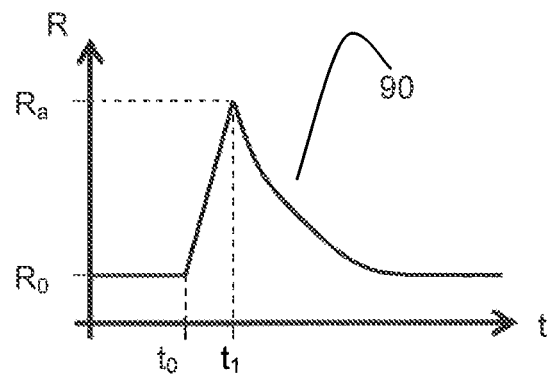
FIGS. 4a and 4b qualitatively show the course of a coupling impedance as measured between subcutaneous electrodes over time for a drug administration and for the case that no drug is administered.
Figure 4B:
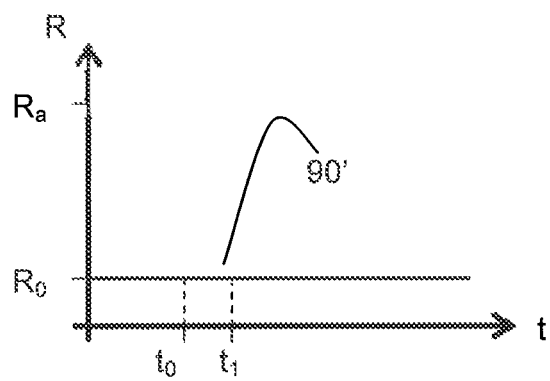

The diagram shown in FIG. 4a shows schematically the course 90 of the impedance value R over time t for a drug administration starting at time $t_0$. In this example, the conductivity of the drug is substantially lower as compared to the conductivity of the interstitial fluid 70, which holds true, for example, for insulin formulations. Accordingly, the impedance value R increases over time when drug administration is started. Depending on the drug amount which is administered, the impedance value R may assume a stationary value which is largely determined by the specific ohmic resistance of the drug. In the exemplary curve shown in FIG. 4, however, the drug amount is too small to fully displace the interstitial fluid, such that the peak administration impedance value $R_a$ is between the interstitial fluid impedance value $R_0$ and the a stationary maximum value that may be assumed if the interstitial fluid is fully displaced. When the drug administration ends at time $t_1$, the impedance value returns to the interstitial fluid impedance value $R_0$ according to a decay curve. The curve 90' in FIG. 4b shows a corresponding case if the drug is not administered for any reason, such as a blocked or leaking infusion cannula 25 or infusion tubing 26, a leaking drug reservoir 20, or a defective drive system 15.

The impedance measuring unit 30 monitors the impedance value R as a function of time t when performing drug administration continuously or in a sampling manner. The event trigger unit 35 detects the occurrence of the temporary impedance value variation and generates an event trigger which is transmitted to the controller unit if the temporary coupling impedance increase does not occur. For the structure and operation of the impedance measuring unit 30 as well as the event trigger unit 35, reference is made to the general description of the invention as given above.

Optionally, the event trigger unit 35 is designed to generate an event trigger if a predefined number of basal drug pulses have not been administered as scheduled as described above in the general description of the invention. For such an embodiment, the diagram in FIG. 5a exemplary shows the administration as a function of time, wherein the upper diagram shows the basal drug pulse volumes V and the lower diagram shows the impedance value. In the upper diagram, the administration of each drug pulse is indicated by an arrow with the length of the arrow indicating the drug pulse amount V (Dirac pulse). The nominal pulse interval Δt is typically in the range of some minutes, e.g., 3 min.

While the first drug pulse 300 is administered as scheduled, the next drug pulse 302 in not administered (indicated by the arrow 302 being dashed) due to sticking of the plug as described above. Instead, it is administered with the following drug pulse 304. After the drug pulse 304, a number of four consecutive drug pulses 306 is administered as scheduled, followed by a number of three consecutive drug pulses 308a, 308b, 308c which are not administered. At the third consecutive drug pulse 308c which is not administered, the event trigger unit generates an event trigger at time T. Here, the number of basal drug pulses which may not be administered without indication an administration anomaly is set to two. As indicated by the lower diagram, each delivery is accompanied by an impedance value pulse 320 while such an impedance value pulse is not present if a drug pulse is not administered. The impedance value pulses 320 are shown qualitatively and generally correspond to the curve shown in FIG. 4a.

Figure 5A:
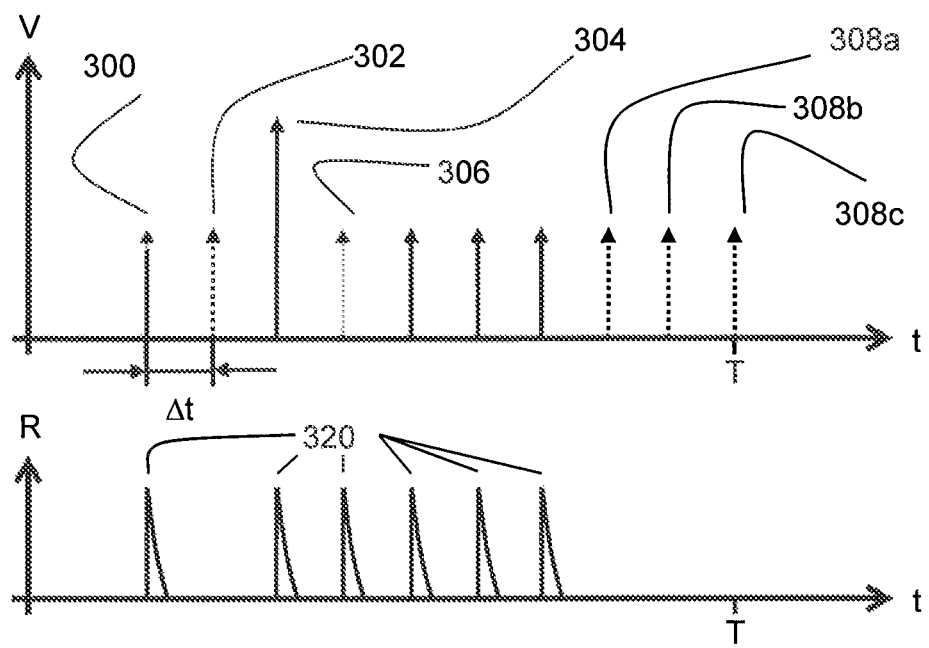
FIGS. 5a and 5b schematically show basal administration and the generation of an event trigger as a function of time for two different basal administration rates.
Figure 5B:
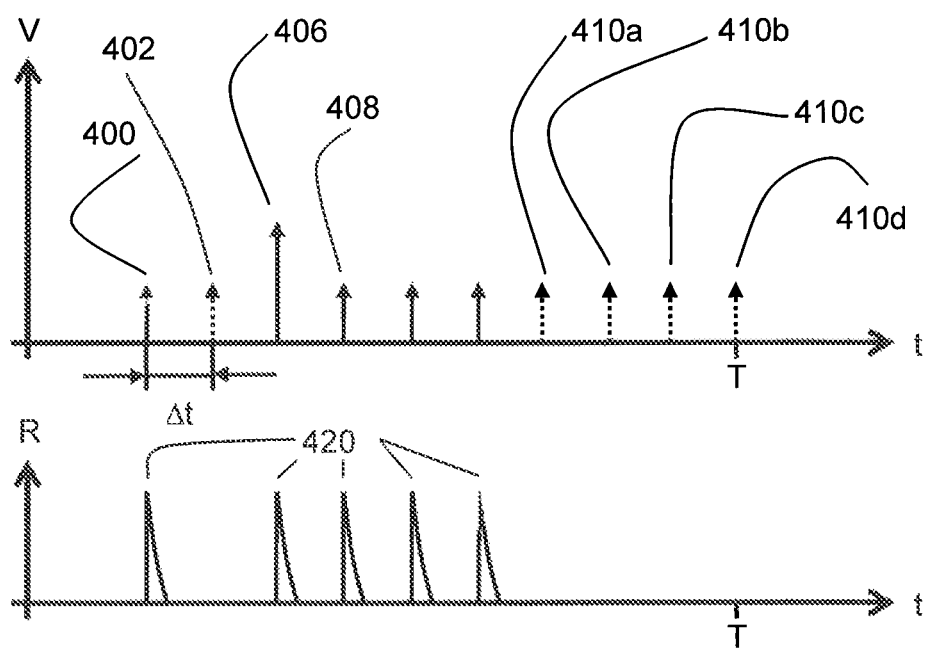

FIG. 5b shows a comparable situation for a substantially smaller administration rate, resulting in smaller basal drug pulses, and the same pulse interval as in FIG. 5a. Here, a larger number of basal drug pulses is likely not to be administered without indication an administration anomaly since the very small increments of the plug displacement result in an increased sticking probability. While drug pulse 400 is administered as scheduled, drug pulse 402 is not administered, but the drug is administered together with the following drug pulse 406, followed by three administered drug pulses 408. The consecutive drug pulses 410a, 410b, 410c 410d are not administered and an event trigger is generated at the scheduled delivery time of the drug pulse 410d. Here, the number of basal drug pulses which may not be administered without indicating an administration anomaly is set to three.

Figure 6:
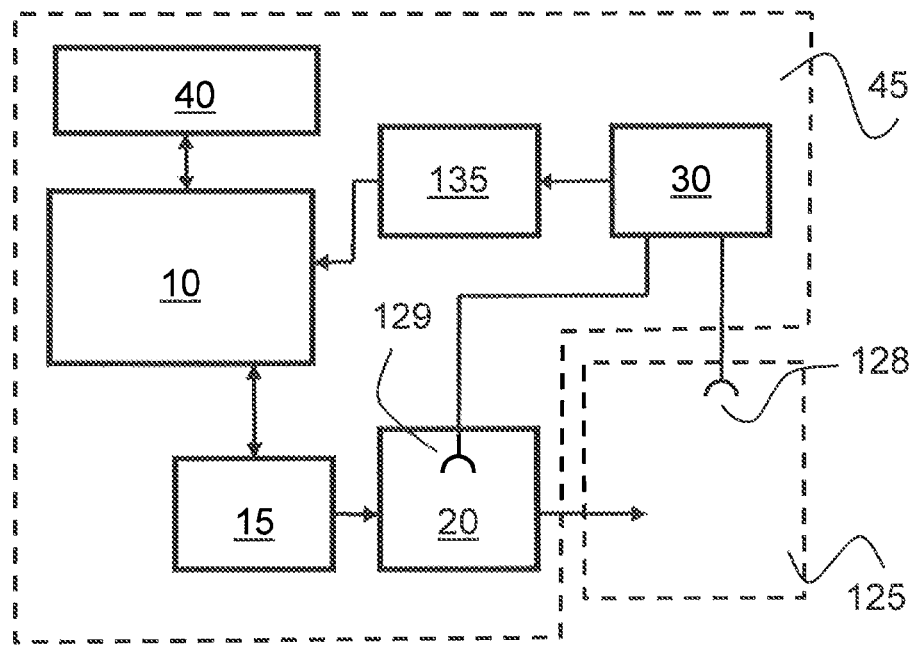
FIG. 6 shows a schematic structural view of a further exemplary infusion device according to one or more embodiments of the present invention.
Figure 7:
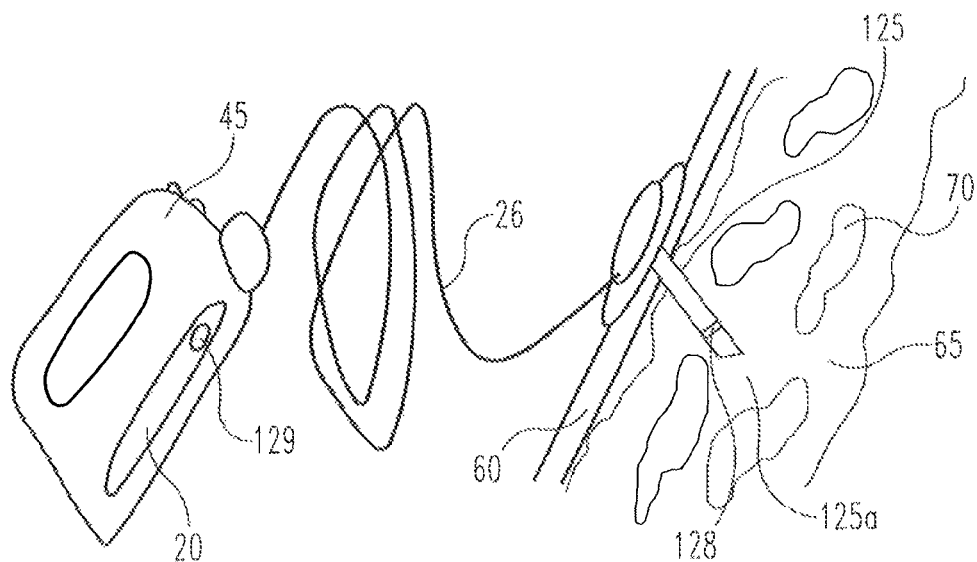
FIG. 7 schematically shows an infusion device according to FIG. 5 during application.

FIG. 6 and FIG. 7 show an ambulatory infusion device according to a further exemplary embodiment of the present invention.

The infusion device comprises a subcutaneous electrode 128, forming a ring-shaped arrangement at the outer surface 84 of the infusion cannula 125. The ambulatory infusion device further comprises an upstream electrode 129 which is arranged upstream of the infusion tubing 26. The upstream electrode 129 may be arranged inside the drug reservoir 20, in particular at an outlet portion of the drug reservoir 20, or between the drug reservoir 20 and the tubing 26, for example in an adapter or connector which couples the drug reservoir 20 and the infusion tubing 26. Under normal operation conditions, the electrodes 128, 129 are coupled by the drug, resulting in an impedance value $R_{drug}$ largely determined by the drug. If, however, there is air present in the infusion tubing 26 and/or the infusion cannula 125, the air may be considered as being in series with the drug as described above. Because the conductivity of air is substantially zero, the impedance value measured between the upstream electrode 129 and the subcutaneous electrode 128 will be substantially infinite in this case. The same effect will occur in case the tubing 26 is blocked by a non-conductive particle, such as a silicone particle from a silicone membrane of the drug reservoir 20. Accordingly, the event trigger unit 135 is designed to compare the impedance value R with a maximum threshold impedance value $R_{max}$ serving as a threshold and to generate an event trigger if the impedance value R exceed the maximum impedance value $R_{max}$. The maximum threshold impedance value $R_{max}$ is somewhat larger than the drug impedance value $R_{drug}$.

The impedance measuring unit 30 may be designed to monitor the impedance value R and the impedance evaluation unit 35 may be designed to evaluate the impedance value R during and/or immediately prior to or after performing a drug administration, but may also be designed to operate substantially continuously or at fixed time intervals of, for example, 1 second, 1 minute, or 3 minutes.

The infusion cannula 125 is made from a non-conductive material, such as Teflon in this exemplary embodiment. For an infusion cannula made from a conductive material, the subcutaneous downstream interruption detection electrode 128 may be a subcutaneous center electrode according to the arrangement shown in FIG. 3. For the structure as well as the operation of the impedance measuring unit 130 as well as the event trigger unit 135, reference is made to the general description of the invention as given above.

Figure 8:
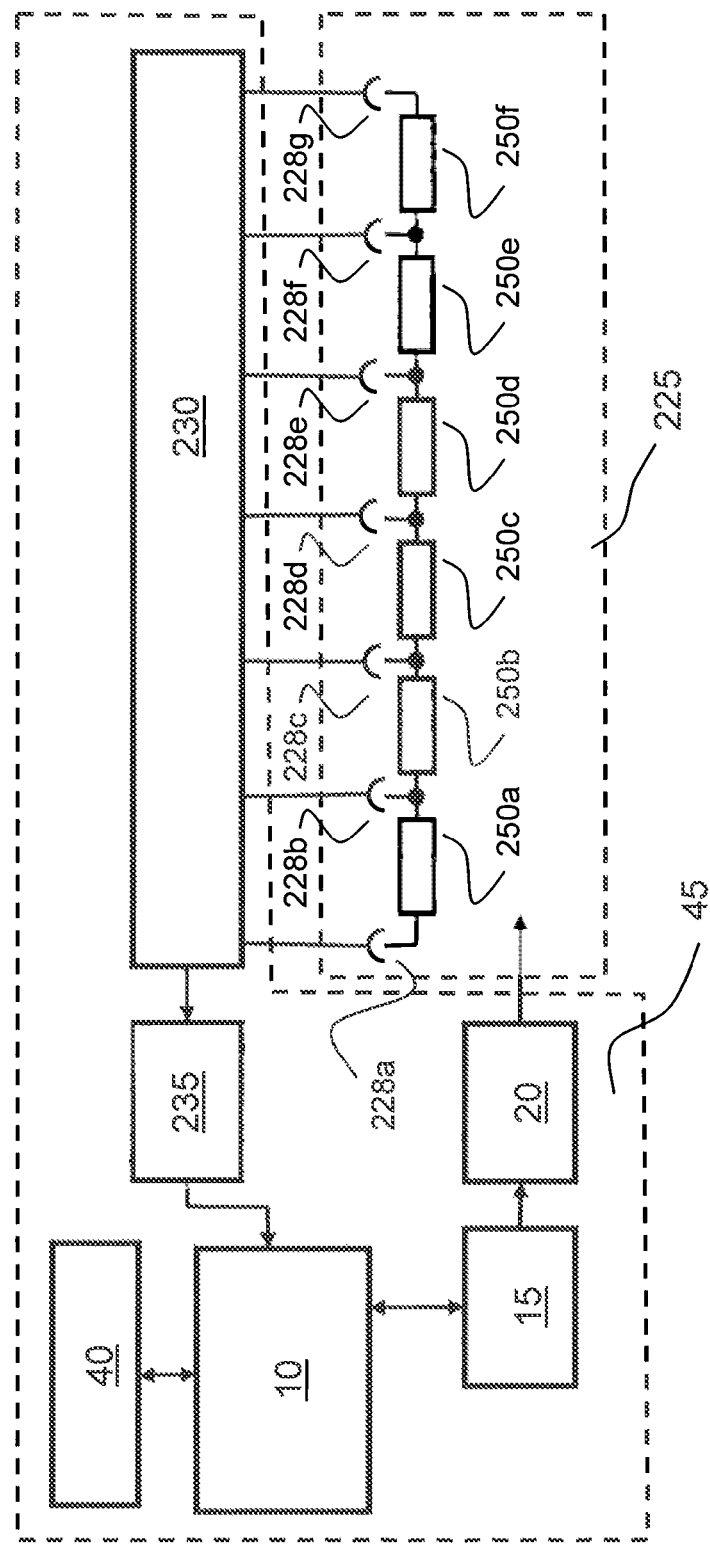
FIG. 8 shows a schematic structural view of a still further exemplary infusion device according to one or more embodiments of the present invention.
Figure 9:
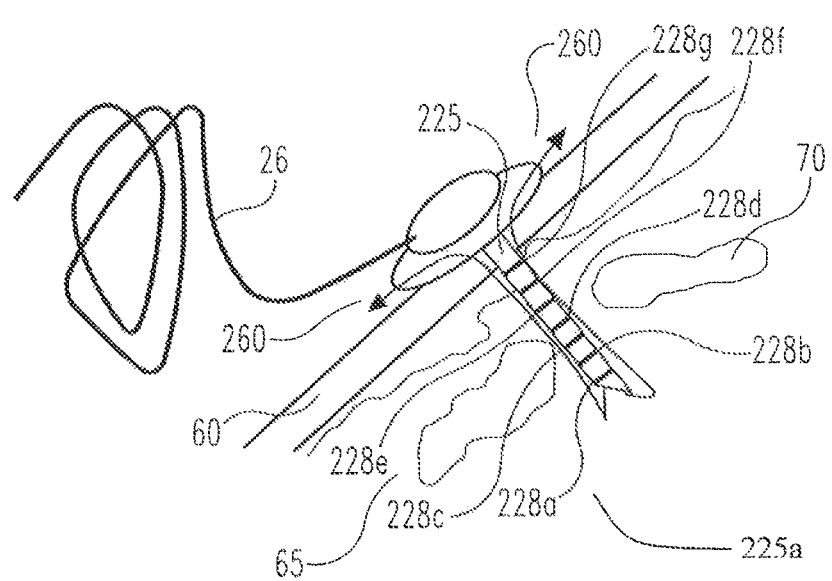
FIG. 9 schematically shows an infusion device according to FIG. 8 during application.

FIG. 8 and FIG. 9 show a still further exemplary embodiment of the present invention. For this type of embodiment, the infusion cannula 225 comprises a set of ring-shaped subcutaneous electrodes 228a-228g which are arranged at the outer surface of the infusion cannula 225 such that they couple via six coupling impedances 250a-250f. While seven gradient measurement electrodes are shown for exemplary purposes, a larger or smaller number may be present as well. As a general rule, a set of n subcutaneous distribution measurement electrodes may be considered as being coupled via n−1 coupling subcutaneous coupling impedances.

Besides detecting if a drug dose is being administered, this type of embodiment is particular advantageous for detecting a flow-back of drug along the cannula 225 and out of the subcutaneous tissue. The arrows 260 indicate drug, in particular insulin, flowing back along the cannula in this way. As may be best seen in FIG. 8, the drug directly couples the subcutaneous electrodes 228-228g in this case, resulting in a uniform impedance distribution along the cannula axis with the impedance values being defined by the drug. Thus, the differences between impedance values coupling neighboring subcutaneous distribution measurement electrodes is substantially reduced or close to zero.

Figure 10A:
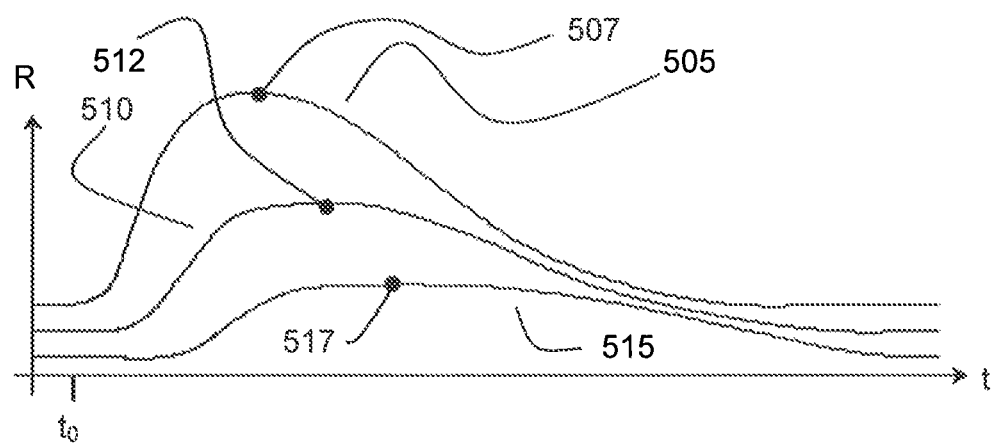
FIGS. 10a and 10b qualitatively show the course of three impedance values as measured at different positions along the cannula axis as a function of time in case of correct administration and in case of drug-flow-back along the cannula axis.
Figure 10B:
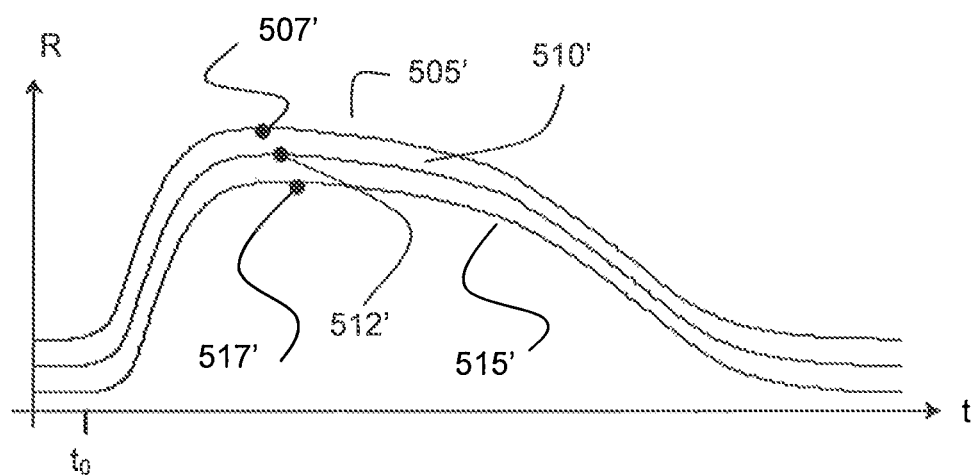

The diagrams FIG. 10a and FIG. 10b qualitatively illustrate the impedance values R as measured by the impedance measuring unit 230 as a function of time t in the case of correct administration and in the case of flow-back. FIG. 10a shows the case of correct administration. For clarity reasons, the diagrams show the courses 505, 510, 515 of only three coupling impedance values, representing, for example the coupling impedance 250a, 250c, and 250f, with curve 505 being the impedance value of the most distal coupling impedance, 250a, curve 510 being the impedance value of the middle coupling impedance 250c and curve 515 being the coupling impedance value of the most proximal coupling impedance 250f. It can be seen that the impedance value increase upon drug administration is largest for the most distal coupling impedance, i.e., the coupling impedance closest to the administration aperture while it is smallest for the most proximal coupling impedance, i.e., the impedance having the largest distance along the cannula axis from the administration aperture. Furthermore, the peak values $R_{max}$, 507, 512, 517 do not occur simultaneously but with increasing delay from the distal cannula tip (curve 515) to the proximal cannula end (curve 505), resulting from the delay of the administered drug reaching the corresponding electrodes. After the end of the drug administration, the curves 505, 510, 515 of the three coupling impedance values return to their initial values. In FIG. 10a as well as in FIG. 10b described below, the three curves are shown with some offset for clarity reasons. In fact, all three initial impedance values may be substantially identical.

FIG. 10b shows the situation of a flow-back of drug along the cannula axis. It can be seen that the curves 505', 510',

515' assume substantially equal peak values 507', 512', 517' in this case. This is due to the fact that the electrodes are directly coupled by the drug in this case.

For the further coupling impedances 250b, 250d, 250e, the corresponding curves lie between the curves shown in FIG. 10a or FIG. 10b, respectively.

For the structure as well as the operation of the impedance measuring unit 230 as well as the event trigger unit 235, reference is made to the general description of the invention as given above.

All documents cited herein are incorporated herein by reference; the citation of any document is not to be construed as an admission that it is prior art with respect to the present invention.

It should be noted that the exemplary embodiments as described above may be used alternatively, but may also be combined, wherein the electrodes, the impedance measuring unit, and the impedance evaluation unit may be fully or partly shared.

REFERENCE SIGNS 10 controller unit
15 drive system
20 drug reservoir
25, 125, 225 infusion cannula
25a, 125a distal cannula tip
26 infusion tubing
28, 29, 128 subcutaneous electrodes
30, 230 impedance measuring unit
35, 135, 235 event trigger unit
40 user interface
45 device housing
50 coupling impedance
60 skin
65 subcutaneous tissue
70 interstitial fluid
80 cannula wall
82 administration aperture
84 cannula outer surface
86 cannula inner surface
90, 90' coupling impedance curve
129 upstream electrode
228a-228g subcutaneous electrodes
250a-250f coupling impedance
260 leaking insulin indication
300, 302, 304, 306, 308, 400, 402, 406, drug pulses
408, 410
320, 420 impedance value pulse
505, 505', 510, 510', 515, 515' impedance value curves
507, 507', 512, 512', 517, 517' impedance peak values
d radial distance
R impedance value
$R_a$ (peak) administration impedance value
$R_0$ interstitial fluid impedance value
$R_{max}$ maximum impedance value
$R_{drug}$ drug impedance value
$\Delta t$ basal pulse time interval
$t_0$ starting time of drug administration
$t_1$ ending time of drug administration
T time of event trigger generation
V drug pulse volume

What is claimed is:

1. An ambulatory infusion device for the infusion of a liquid drug into a patient's body over an extended time period, comprising:

a) an infusion cannula designed to be placed in the patient's subcutaneous tissue;
b) at least two subcutaneous electrodes, the at least two subcutaneous electrodes being comprised by the infusion cannula and being placeable in the subcutaneous tissue;
c) an impedance measuring unit, the impedance measuring unit being operatively coupled to the at least two electrodes and configured to measure at least one impedance value between the at least two electrodes, a variation of the at least one impedance value reflecting a displacement of interstitial fluid by drug upon drug administration;
d) an event trigger unit operatively coupled to the impedance measuring unit and being configured to evaluate the at least one impedance value and to generate an event trigger if evaluation of the at least one impedance value indicates the occurrence of an administration anomaly.

2. The ambulatory infusion device according to claim 1, wherein the infusion device is configured to administer consecutive drug pulses, the impedance measuring unit is configured to measure consecutive impedance values, and wherein the event trigger unit is configured to generate an event trigger if evaluation of the consecutive impedance values indicates that a predefined number of consecutive drug pulses have not been administered.

3. The ambulatory infusion device according to claim 1, wherein the impedance measuring unit is configured to monitor the at least one impedance value as a function of time and/or position and wherein the event trigger unit is configured to generate an event trigger if the at least one impedance value as a function of time and/or position indicates the occurrence of an administration anomaly.

4. The ambulatory infusion device according to claim 3, wherein the event trigger unit is configured to detect the presence or absence of a characteristic temporary impedance value variation upon drug administration and to generate an event trigger in case of the absence of the temporary impedance value variation.

5. The ambulatory infusion device according to claim 1 further comprising a subcutaneous center electrode and a subcutaneous counter electrode, the subcutaneous center electrode being arranged in the center of an administration aperture of the infusion cannula and the subcutaneous counter electrode being arranged at the infusion cannula in a distance from the subcutaneous center electrode.

6. The ambulatory infusion device according to claim 1 further comprising a set of at least three subcutaneous electrodes.

7. The ambulatory infusion device according to claim 6, wherein the at least three subcutaneous electrodes are comprised by the infusion cannula at different axial positions along the cannula axis.

8. The ambulatory infusion device according to claim 6, wherein the impedance measuring unit is configured to measure at least two impedance values between the at least three subcutaneous electrodes.

9. The ambulatory infusion device according to claim 8, wherein the event trigger unit is configured to detect if the at least two impedance values indicate the presence of a characteristic non-uniform impedance distribution along the cannula axis resulting from drug administration and to generate an event trigger if the at least two impedance values indicate the absence of the characteristic non-uniform impedance distribution.

10. The ambulatory infusion device according to claim 1 further comprising an upstream electrode arranged upstream from the infusion cannula.

11. Use of an infusion cannula in an ambulatory infusion device according to claim 1, for subcutaneous drug infusion over an extended time period, wherein the infusion cannula comprises the at least two subcutaneous electrodes.

12. A method for administration supervision in an ambulatory infusion device for subcutaneous drug infusion over an extended time period, comprising the steps of:
   a) measuring by an impedance measuring unit at least one impedance value between at least two subcutaneous electrodes, the at least two subcutaneous electrodes being comprised by an infusion cannula, a variation of the at least one impedance value reflecting a displacement of interstitial fluid by drug upon drug administration;
   b) generating by an event trigger unit an event trigger if an evaluation of the at least one impedance value indicates the occurrence of an administration anomaly.

13. The method for administration supervision according to claim 12 further comprising generating an event trigger if the impedance value evaluation indicates that a predefined number of consecutive drug pulses has not been administered.

14. The method for administration supervision according to claim 12 further comprising detecting the presence of a characteristic temporary impedance value variation upon drug administration and generating an event trigger in case of the absence of the temporary impedance value variation.

15. The method for administration supervision according to claim 12 further comprising detecting the presence of a characteristic non-uniform impedance distribution along the cannula axis resulting from drug administration and generating an event trigger in case of the absence of the characteristic non-uniform impedance distribution.

* * * * *

UNITED STATES PATENT AND TRADEMARK OFFICE
CERTIFICATE OF CORRECTION

PATENT NO. : 9,504,787 B2
APPLICATION NO. : 12/641911
DATED : November 29, 2016
INVENTOR(S) : Reto Aeschilimann et al.

It is certified that error appears in the above-identified patent and that said Letters Patent is hereby corrected as shown below:

In the Specification

Column 5, Line 43:
"suring unit and may also the event trigger unit are designed"
Should read:
--suring unit and also the event trigger unit are designed--;

Column 7, Line 8:
"The event trigger unit may further detect an temporary"
Should read:
--The event trigger unit may further detect a temporary--;

Column 7, Line 10:
"at least one impedance value temporarily exceeds an thresh-"
Should read:
--at least one impedance value temporarily exceeds a thresh- --;

Column 7, Line 26:
"being arranged at the infusion cannula in an distance from"
Should read:
--being arranged at the infusion cannula in a distance from--;

Column 9, Line 27:
"hand and a flow-back on the other hand and may be"
Should read:
--hand and a flow-back on the other hand may be--;

Signed and Sealed this
Fifth Day of September, 2017

Joseph Matal
*Performing the Functions and Duties of the*
*Under Secretary of Commerce for Intellectual Property and*
*Director of the United States Patent and Trademark Office*

CERTIFICATE OF CORRECTION (continued)
U.S. Pat. No. 9,504,787 B2

Column 10, Line 7:
"been not administered."
Should read:
--been administered.--;

Column 12, Line 24:
"such as Teflon. In this, case, the subcutaneous counter"
Should read:
--such as Teflon. In this case, the subcutaneous counter--;

Column 12, Line 29:
"course 90 of the impedance value R over time t for a drug"
Should read:
--course 90 of the impedance value R over time T for a drug--;

Column 12, Line 42:
"value $R_0$ and the a stationary maximum value that may be"
Should read:
--value $R_0$ and a stationary maximum value that may be--;

Column 12, Line 52:
"ance value R as a function of time t when performing drug"
Should read:
--ance value R as a function of time T when performing drug--;

Column 13, Line 17:
"be administered without indication an administration"
Should read:
--be administered without indication of an administration--;

Column 13, Line 27:
"administered without indication an administration anomaly"
Should read:
--administered without indication of an administration anomaly--;

Column 14, Line 28:
"this type of embodiment is particular advantageous for"
Should read:
--this type of embodiment is particularly advantageous for--; and Column 14, Line 40:
"measuring unit 230 as a function of time t in the case of"
Should read:
--measuring unit 230 as a function of time T in the case of--.